United States Patent [19]

Fukuda et al.

[11] Patent Number: 4,904,590
[45] Date of Patent: Feb. 27, 1990

[54] ANTIBIOTIC A80915 AND PROCESS FOR ITS PRODUCTION

[75] Inventors: David S. Fukuda, Brownsburg; Jon S. Mynderse, Indianapolis; Raymond C. Yao, Carmel, all of Ind.

[73] Assignee: Eli Lilly and Company, Indianapolis, Ind.

[21] Appl. No.: 290,724

[22] Filed: Dec. 27, 1988

[51] Int. Cl.$^4$ .................. C12P 7/24; C12R 1/465; C07D 311/92; A61K 31/35
[52] U.S. Cl. .................. 435/147; 435/148; 435/822; 435/886; 549/389; 514/454
[58] Field of Search .............. 435/822, 886, 147, 148; 549/389; 514/454

[56] References Cited

U.S. PATENT DOCUMENTS 4,587,218  5/1986  Hershberger ............... 435/252.6
4,713,331  12/1987  Michel et al. ............... 435/68

OTHER PUBLICATIONS

K. Shiomi et al., "Structures of New Antibiotics Napyradiomycins", *The Journal of Antibiotics*, vol. 39, No. 4, Apr. 1986, pp. 494–501.
K. Shiomi et al., "Novel Antibiotics Napyradiomycins Production, Isolation, Physico-Chemical Properties and Biological Activity", *The Journal of Antibiotics*, vol. 39, No. 4, Apr. 1986, pp. 487–493.
K. Shiomi et al., "New Antibiotic Napyradiomycins A2 and B4 and Stereochemistry of Napyradiomycins", *The Journal of Antibiotics*, vol. 40, No. 9, Sep. 1987, pp. 1213–1219.
S. Gomi et al., "Studies on New Antibiotics SF2415. II. The Structural Elucidation", *The Journal of Antibiotics*, vol. 40, No. 6, Jun. 1987, pp. 740–749.
T. Shomura et al., "Studies on New Antibiotics SF2415. I. Taxonomy, Fermentation, Isolation, Physico-Chemical Properties and Biological Activities", *The Journal of Antibiotics*, vol. 40, No. 6, Jun. 1987, pp. 732–739.

Primary Examiner—Ronald W. Griffin
Assistant Examiner—Pamela S. Webber
Attorney, Agent, or Firm—Joseph A. Jones; Leroy Whitaker

[57] ABSTRACT

New antibiotic A80915 and its dehydrochlorination derivatives are useful antibacterial agents. Methods of making antibiotic A80915 by culture of *Streptomyces aculeolatus*, NRRL 18422, and compositions containing an A80915 antibiotic also are provided.

18 Claims, No Drawings

ANTIBIOTIC A80915 AND PROCESS FOR ITS PRODUCTION

SUMMARY OF THE INVENTION

This invention relates to the new antibiotic A80915 comprising several individual components including A80915A, A80915B, A80915C, and A80915D, and to a new strain of *Streptomyces aculeolatus*, NRRL 18422, which produces this antibiotic.

This invention also relates to dehydrochlorination derivatives of A80915.

Another aspect of this invention is a process for producing antibiotic A80915 by cultivating *Streptomyces aculeolatus*, NRRL 18422, under submerged aerobic fermentation conditions until a substantial level of the antibiotic is produced. A80915 is extracted from the fermentation broth and from the mycelium with organic solvents. A80915 is separated, further purified, and the individual components isolated by conventional techniques.

Because *Streptomyces aculeolatus*, NRRL 18422, is a newly discovered strain, this invention further provides a biologically pure culture of this microorganism or an A80915-producing mutant, variant or recombinant thereof.

A80915 is a useful antibacterial agent having gram-positive activity. In addition, A80915 has antifungal activity. Methods and compositions pertaining to these uses also are provided.

The A80915 antibiotics also are useful as intermediates in the preparation of other antibiotic compounds.

DETAILED DESCRIPTION OF THE INVENTION

Although many beneficial antibiotics are available, there is a continuing need to find improved antibiotics for human and animal medicine.

This invention relates to a new group of antibiotics, the A80915 antibiotics. Antibiotic A80915 comprises several individual components. Components A80915A, A80915B, A80915C and A80915D have the structures shown in formulas 1 to 4.

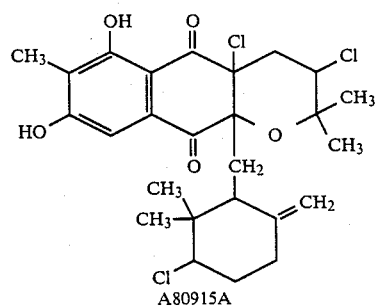

A80915A

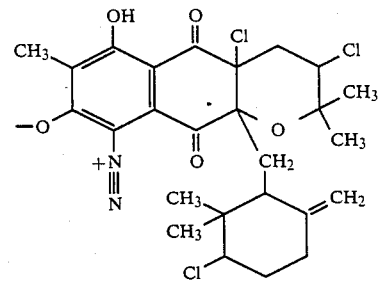

A80915B

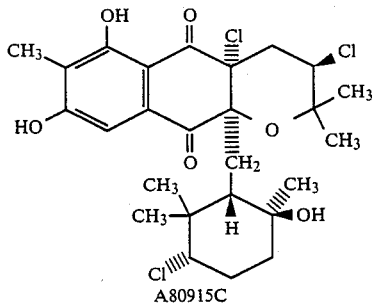

A80915C

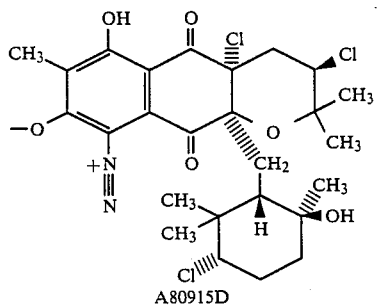

A80915D

Antibiotic A80915 is structurally related to the napyradiomycins [K. Shiomi, H, Nakamura, H. Inuma, H. Naganawa, K. Isshiki, T. Takeuchi, and H. Umezawa, "Structures of New Antibiotics Napyradiomycins", *J. Antibiotics* 39, 494–501 (1986)] and the SF2415 antibiotics [S. Gomi, S. Ohuchi, T. Sakaki, J. Itoh, and M. Sezaki, "Studies on New Antibiotics. SF2415", *J. Antibiotics* 40, 740–749 (1987)]. Minor amounts of napyradiomycin B1 are co-produced along with antibiotic A80915 during cultivation of *Streptomyces aculeolatus*, NRRL 18422.

In this discussion the term "A80915 antibiotic" will denote a member selected from the group consisting of antibiotic A80915 and its individual components and derivatives. The term "antibiotic A80915" denotes the A80915 components that are produced by cultivating *Streptomyces aculeolatus*, NRRL 18422.

Characteristics of A80915

The A80915 components have the following characteristics:

| A80915A | | |
|---|---|---|
| Molecular formula: $C_{26}H_{31}Cl_3O_5$ | | |
| Mass spectrometry (FABMS): m/z 529, 531, 533 (M + H isotopic cluster) | | |
| Ultraviolet $\lambda_{max}$(EtOH): | Neutral | 266 nm, $\epsilon$17333 |
| | | 332 nm, $\epsilon$7353 |
| | Acid | 266 nm, $\epsilon$17356 |
| | | 330 nm, $\epsilon$7320 |
| | Base | 246 nm, $\epsilon$13495 |
| | | 300 nm, $\epsilon$15090 |
| | | 401 nm, $\epsilon$13486 |

$^1$H NMR (270 MHz, CDCl$_3$): 12.34 (bs), 7.38 (s), 4.78 (bs), 4.47 (dd), 3.75 (dd), 2.68 (dd), 2.55 (dd), 2.36 (dd), 2.27 (s), 2.24 (m), 2.04 (d), 1.95 (m), 1.73 (m), 1.62 (d), 1.39 (s), 1.20 (s), 0.66 (s), 0.57 (s) ppm.

$^{13}$C NMR (67.9 MHz, CDCl$_3$): 194.60 (s), 194.15 (s), 163.23 (s), 161.78 (s), 145.43 (s), 131.59 (s), 120.13 (s), 110.13 (t), 108.16 (s), 107.69 (d), 84.11 (s), 81.17 (s), 78.81 (s), 70.68 (d), 59.79 (d), 45.90 (d), 42.90 (t), 41.72 (s), 35.56 (t), 35.07 (t), 34.55 (t), 28.96 (q), 26.42 (q), 22.49 (q), 15.45 (q), 8.24 (q) ppm.

| A80915B | | |
|---|---|---|
| Molecular formula: $C_{26}H_{29}Cl_3N_2O_5$ | | |
| Mass spectrometry (FABMS): m/z 555, 557, 559 | | |
| (M + H isotopic cluster) | | |
| Ultraviolet $\lambda_{max}$(EtOH): | Neutral | 259 nm $\epsilon$12458 |
| | | 301 nm $\epsilon$10317 |
| | | 366 nm $\epsilon$4684 |
| | Acid | 258 nm $\epsilon$12817 |
| | | 301 nm $\epsilon$9936 |
| | | 361 nm $\epsilon$3925 |
| | Base | 265 nm $\epsilon$15303 |
| | | 306 nm $\epsilon$14327 |
| | | 395 nm $\epsilon$7783 |

$^1$H NMR (270 MHz, CDCl$_3$): 4.81 (bs), 4.59 (bs), 4.41 (dd), 3.76 (dd), 2.55 (dd), 2.50 (dd), 2.39 (dd), 2.13 (s), 2.03 (m), 2.03 (m), 1.78 (d), 1.68 (m), 1.66 (d), 1.44 (s), 1.19 (s), 0.99 (s), 0.66 (s) ppm.

$^{13}$C NMR (62.9 MHz, CDCl$_3$): 192.27 (s), 192.19 (s), 173.61 (s), 167.17 (s), 145.35 (s), 135.10 (s), 123.00 (s), 111.33 (s), 110.38 (t), 83.79 (s), 79.41 (s), 79.41 (s), 77.46 (s), 69.91 (d), 57.97 (d), 46.78 (d), 43.07 (t), 42.84 (s), 37.39 (t), 35.58 (t), 34.69 (t), 28.87 (q), 26.45 (q), 22.40 (q), 15.37 (q), 9.09 (q) ppm.

| A80915C | | |
|---|---|---|
| Molecular formula: $C_{26}H_{33}Cl_3O_6$ | | |
| Mass spectrometry (FABMS): 547, 549, 551 | | |
| (M + H isotopic cluster) | | |
| Ultraviolet $\lambda_{max}$(EtOH): | Neutral | 267 nm, $\epsilon$19495 |
| | | 314 nm, $\epsilon$9428 |
| | | 356 nm, $\epsilon$7891 |
| | Acid | 266 nm, $\epsilon$22552 |
| | | 331 nm, $\epsilon$8857 |
| | Base | 246 nm, $\epsilon$15454 |
| | | 304 nm, $\epsilon$21058 |
| | | 400 nm, $\epsilon$15220 |

$^1$H NMR (270 MHz, CDCl$_3$): 12.27 (bs), 10.33 (bs), 7.96 (s), 6.55 (s), 4.58 (dd), 3.42 (dd), 2.64 (dd), 2.56 (dd), 2.47 (dd), 2.22 (s), 1.96 (m), 1.88 (m), 1.76 (m), 1.65 (d), 1.57 (s), 1.41 (d), 1.36 (s), 1.33 (s), 0.86 (s), 0.42 (s) ppm.

$^{13}$C NMR (62.9 MHz, CDCl$_3$): 192.67 (s), 191.02 (s), 164.36 (s), 163.39 (s), 131.95 (s), 120.43 (s), 108.72 (d), 107.18 (s), 85.69 (s), 81.56 (s), 80.42 (s), 72.30 (s), 71.08 (d), 57.98 (d), 52.30 (s), 42.16 (t), 40.66 (s), 40.61 (t), 38.30 (t), 29.69 (t), 29.28 (q), 28.55 (q), 24.43 (q), 22.97 (q), 15.69 (q), 6.40 (q) ppm.

| A80915D | | |
|---|---|---|
| Molecular formula: $C_{26}H_{31}Cl_3N_2O_6$ | | |
| Mass spectrometry (FDMS): m/z 573, 575, 577 | | |
| (M + H isotopic cluster) | | |
| Ultraviolet $\lambda_{max}$(EtOH): | Neutral | 261 nm, $\epsilon$16678 |
| | | 305 nm, $\epsilon$15173 |
| | | 403 nm, $\epsilon$4863 |

$^1$H NMR (270 MHz, CDCl$_3$): 11.34 (bs), 4.61 (bs), 4.50 (dd), 3.68 (dd), 2.77 (dd), 2.62 (dd), 2.46 (dd), 2.15 (s), 2.01 (m), 1.90 (m), 1.78 (m), 1.61 (dd), 1.56 (s), 1.47 (dd), 1.30 (s), 1.21 (s), 0.75 (s), 0.51 (s) ppm.

$^{13}$C NMR (62.9 MHz, CDCl$_3$): 192.00 (s), 190.30 (s), 173.28 (s), 160.01 (s), 133.31 (s), 124.23 (s), 111.08 (s), 83.62 (s), 82.90 (s), 80.44 (s), 76.52 (s), 70.53 (s), 70.44 (d), 57.27 (d), 50.12 (d), 42.86 (t), 41.39 (t), 40.95 (s), 38.33 (t), 30.63 (t), 28.68 (q), 28.54 (q), 24.63 (q), 22.48 (q), 16.22 (q), 9.28 (q) ppm.

Antibiotic A80915 is produced by a culture of an A80915-producing strain of *Streptomyces aculeolatus*, NRRL 18422, as described herein. The antibiotic is produced under submerged aerobic conditions in a suitable culture medium; it can be recovered from the culture medium, purified, and the individual components isolated by using various isolation and purification procedures understood in the art.

Culture A80915 was isolated from a soil sample from the Palau Islands.

A culture of the A80915-producing organism has been deposited and made part of the stock culture collection of the Midwest Area Northern Regional Research Center, Agricultural Research Service, U.S. Department of Agriculture, 1815 North University Street, Peoria, Illinois 61604, from which it is available to the public under the accession number NRRL 18422.

Taxonomic studies of this organism were carried out by Frederick P. Mertz of the Lilly Research Laboratories. Based on these studies and comparison with the published descriptions of other species, the organism is classified as a strain of *Streptomyces aculeolatus*.

Methods Used

The methods recommended by the International Streptomyces Project (ISP) for the characterization of Streptomyces species [E. B. Shirling and D. Gottlieb, "Methods for Characterization of Streptomyces Species", *Int. J. Syst. Bacteriol.* 16(3), 313–340 (1966)] have been followed.

Melanoid pigment production (chromogenicity) was determined with ISP No. 1 (tryptone-yeast extract broth), ISP No. 6 (peptone-yeast extract iron agar), and ISP No. 7 (tyrosine agar).

Morphology was studied using an optical light microscope. A scanning electron microscope (SEM) was used to study the spore surface ornamentation.

ISCC-NBS Centroid Color Charts, standard sample No. 2106 (National Bureau of Standards, 1958, U.S. Department of Commerce, Washington, D.C.) and the Color Harmony Manual (4th ed., Color Standards Department, Container Corporation of America, Chicago, Illinois, 1958) were used to assign color names to the reverse side and aerial spore mass respectively.

The isomers of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates", *Appl. Microbiol.* 12, 421–423 (1964)] and of Lechevalier [M. P. Lechevalier, and H. Lechevalier, "Chemical Composition as a Criterion in the Classification of Aerobic Actinomycetes", *Int. J. Syst. Bacteriol.* 20, 435–443 (1970)].

Cultural Characteristics

Culture A80915 grew only moderately on complex and defined media. Aerial hyphae were moderately produced on a limited number of media. The aerial spore mass was white to pale yellow. The reverse side was yellow-brown to orange. A distinctive red pigment was observed on a few of the media. A light reddish-brown pigment was released into the medium on some of the media used. These cultural characteristics are presented in Table No. 1.

Morphological Characteristics

Normal substrate mycelia with no fragmentation were observed. Aerial hyphae had short chains of spores arranged as hooks and loops, with some spirals. The general morphology was Retinaculum-apertum. The spore surface ornamentation was warty. The spores were spherical in shape and averaged 0.6 to 0.8 µm in size. The spore chain appeared to be between 10 to 50 spores in length. No sclerotia, sporangia, or motile cells were observed.

Physiological Characteristics

Culture A80915 utilized L-arabinose, fructose, galactose, glucose, mannitol, raffinose, L-rhamnose, salicin and xylose. It did not utilize inositol and sucrose. The production of melanoid pigments is doubtful. A light reddish-brown pigment was produced in ISP media 1, 6, and 7, but this was not considered to be melanin. $H_2S$ is not produced. A80915 liquefied gelatin, reduced nitrate, and hydrolyzed, but did not peptonize skim milk. Starch and calcium malate were hydrolyzed. A80915 grew in a very narrow temperature range of 20° to 30° C. It tolerated levels of NaCl up to 5%.

culture *S. aculeolatus* is not listed in the Approved Lists of Bacterial Names [V. B. D. Skerman, V. McGowan, and P. H. A. Sneath, 1980, "Approved Lists of Bacterial Names", American Society for Microbiology, Washington, D.C.], nor has it been validly published.

A80915 was compared to the napyradiomycin producing culture *Chainia rubra* MG801-AF1 [K. Shiomi, H. Iinuma, M. Hamada, H. Naganawa, M. Manabe, C. Matsuki, T. Takeuchi, and H. Umezawa, "Novel antibiotics napyradiomycins production, isolation, physicochemical properties and biological activity", *J. Antibiotics* 39, 487–493 (1986)], and the tetronomycin producing culture Streptomyces sp. nov. S53161/A [C. Keller-Juslen, H. D. King, M. Kuhn, H. R. Loosli, W. Pasche, T. J. Petcher, H. P. Weber, and A. von Wartburg, "Tetronomycin, a novel polyether of unusual structure", *J. Antibiotics* 35, 142–150 (1982)]. These comparisons indicated A80915 to be very similar to *C. rubra* MG802-AF1 with the exception that no sclerotia were observed in any media on which A80915 was grown. Since the presence of these special morphological properties are characteristic of the genus Chainia, A80915 was not classified in this genus. The tetronomycin producing culture Streptomyces sp. nov. S5316/A was not as close in morphological or physiological characteristics to A80915 as was *S. aculeolatus*.

TABLE NO. 1

| Cultural characteristics of A80915 at 30°C. and 14 days incubation. | | | | | |
|---|---|---|---|---|---|
| Medium | Growth | Reverse Color | Aerial Growth | Mycelium Color | Soluble Pigment |
| ISP[1] medium 2 | poor | 74. s.y-Brown | none | none | none |
| ISP medium 3 | good | 54. br-Orange | poor | white to pY | l. r-Brown |
| ISP medium 4 | abundant | 58. m-Brown | fair | white | none |
| ISP medium 5 | good | 58. m-Brown | none | none | none |
| ISP medium 7 | good | 43. m. r-Brown | none | none | r-Orange |
| Anio-Hensens | good | 76. l. y-Brown | good | white to pY | none |
| Calcium malate | fair | 77. m. y-Brown | none | none | none |
| Czapek's | good | 70. l. o-Yellow | good | white to pY | none |
| GAA[2] | fair | 17. v. d. Red | fair | white | none |
| Glycerol-glycine | abundant | 44. d. r-Brown | none | none | l. r-Brown |
| Potato-carrot | good | 71. m. o-Yellow | good | white to pY | none |
| TPO[3] | abundant | 51. deep Orange | none | none | l. r-Orange |
| Tap water agar | fair | 73. p. o-Yellow | fair | white to pY | none |

[1] International Streptomyces Project
[2] Glucose Asparagine Agar
[3] Tomato Paste Oatmeal

Cell-Wall Analysis

Hydrolyzed whole cells contain mesodiaminopimelic acid. The diagnostic sugars in the whole cell extracts are galactose, glucose, and ribose. Thus, A80915 has a Type I cell wall, and a noncharacteristic (NC) sugar pattern.

Identity of A80915

Culture A80915 belongs in the genus Streptomyces and is similar to the SF2415 producing culture *S. aculeolatus* [T. Shomura, S. Gomi, M. Ito, J. Yoshida, E. Tanaka, S. Amano, H. Watabe, S. Ohuchi, J. Itoh, and M. Sezaki, "Studies on new antibiotics SF2415 I. Taxonomy, Fermentation, Isolation, Physico-chemical properties and biological activities", *J. Antibiotics* 40, 732–739 (1987)]. A taxonomic comparison of these two cultures are listed in Table No. 2. They differed only in temperature range, tolerance of NaCl, and the ability to reduce nitrates. These differences are considered to be strain and not species differences. Therefore, A80915 is classified as a strain of *Streptomyces aculeolatus*. The

TABLE NO. 2

| Taxonomic comparison of similarities and differences between A80915 and *Streptomyces aculeolatus*. | | |
|---|---|---|
| Characteristic | A80915 | S. aculeolatus |
| Aerial color | W (Y) | W (Y) |
| Reverse color | y-Brown to O | y-Brown to O |
| Soluble pigment | reddish brown | reddish brown |
| Morphology | RA (S) | RA (S) |
| Temperature range °C. | 20–30 | 15–37 |
| NaCl tolerance | 5% | 3–4% |
| Gelatin liquefaction | + | + |
| Melanoid pigments | | |
| ISP 1 | − | − |
| ISP 6 | − | − |
| ISP 7 | − | − |
| Nitrate reduction | + | − |
| Starch hydrolysis | + | + |
| Peptonization of milk | − | − |
| Carbohydrate utilization | | |
| L-arabinose | + | + |
| fructose | + | + |

TABLE NO. 2-continued

Taxonomic comparison of similarities and
differences between A80915 and
*Streptomyces aculeolatus.*

| Characteristic | A80915 | S. aculeolatus |
|---|---|---|
| glucose | + | + |
| inositol | − | − |
| mannitol | + | + |
| raffinose | + | + |
| L-rhamnose | + | + |
| sucrose | − | − |
| xylose | + | + |
| Formation of sclerotia | − | − |
| Spore surface | warty | warty |
| Spore shape | spherical | ellipsoidal |

As is the case with other organisms, the characteristics of the A80915-producing culture *Streptomyces aculeolatus*, NRRL 18422, are subject to variation. Recombinants, mutants or variants of the strain may be obtained by methods known in the art. For example, mutants can be obtained by treatment with various known physical and chemical mutagens such as ultraviolet light, X rays, gamma rays and chemicals such as N-methyl-N'-nitro-N-nitrosoguanidine. All natural and induced variants, mutants and recombinants of this *Streptomyces aculeolatus* strain which retain the characteristic of A80915 production are part of this invention.

The culture medium used to grow *Streptomyces aculeolatus*, NRRL 18422, can be any one of a number of media. For economy in production, optimal yield, and ease of product isolation, however, certain culture media are preferred. For example, a preferred carbohydrate source in large-scale fermentation is glucose, although blackstrap molasses, starch and the like can also be used.

Preferred nitrogen sources are Bacto peptone or enzyme-hydrolyzed casein, although other nitrogen sources should also be useful.

Among the nutrient inorganic salts which may advantageously be incorporated in the culture media are the customary soluble salts capable of yielding zinc, sodium, magnesium, calcium, ammonium, chloride, carbonate, sulfate, nitrate and like ions.

The presence of phosphate in the culture medium appears to inhibit the A80915 biosynthesis. Therefore, media containing only low levels of phosphate are preferred.

Essential trace elements necessary for the growth and development of the organism should also be included in the culture medium. Such trace elements commonly occur as impurities in other substituents of the medium in amounts sufficient to meet the growth requirements of the organism. If foaming is a problem, small amounts (i.e. 0.2 ml/L) of an antifoam agent such as polypropylene glycol may be added to large scale fermentation media if needed.

For production of substantial quantities of antibiotic A80915, submerged aerobic fermentation in tanks is preferred. Small quantities of A80915 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80915 is produced by *Streptomyces aculeolatus*, when grown at temperatures between about 20° and about 35° C. A good temperature for A80915 production appears to be about 30° C.

As is customary in submerged aerobic culture processes, sterile air is blown into the vessel from the bottom while the medium is stirred with conventional turbine impellors. In general, the aeration rate and agitation rate should be sufficient to maintain the level of dissolved oxygen at or above 30% of saturation.

Production of antibiotic A80915 can be followed during the fermentation by testing samples of the broth for antibiotic activity against organisms known to be sensitive to the antibiotic. One assay organism useful in testing A80915 is *Bacillus subtilis* ATCC 6633. The bioassay is conveniently performed by the agar-well or disc plate assay.

Following its production under submerged aerobic fermentation conditions, A80915 can be recovered from the fermentation medium by methods used in the fermentation art. The antibiotic activity produced during fermentation of the A80915-producing organism occurs both in the mycelia and the broth. This activity may be recovered by extraction of the whole broth. Maximum recovery of A80915 is accomplished, however, by initially filtering the medium to separate the broth from the mycelial mass. The filtered broth and the mycelial mass can then be purified separately to give their respective portion of A80915. A variety of techniques may be used in this purification.

A preferred technique for purification of the filtered broth involves extraction with a suitable solvent such as, for example, ethyl acetate. The extracting solvent can then be evaporated under vacuum to give the broth portion of A80915. Alternatively, A80915 can be recovered from the broth by adsorption on nonionic macroreticular resins such as Diaion HP-20 (Mitsubishi) and eluted with suitable aqueous organic solvent mixtures, for example, water:acetonitrile, water:methanol or water:acetone.

A preferred method of purifying the mycelial mass is to extract the separated mycelial filter cake with a suitable solvent such as, for example, acetone or methanol. The extracting solvent then is evaporated under vacuum to give a concentrated aqueous solution. This aqueous solution is extracted with a suitable solvent such as, for example, ethyl acetate. The extracting solvent is concentrated under vacuum to give the mycelial portion of A80915.

The broth and mycelial portions of A80915 are further purified by similar procedures. Purification of antibiotic A80915 and isolation of the components can be accomplished by conventional techniques such as high performance liquid chromatography (HPLC), column chromatography or preparative thin layer chromatography (TLC). Convenient column chromatography systems include Sephadex LH-20 (Pharmacia) eluted with organic solvent mixtures such as chloroform:methanol, and the like, or silica gel eluted with solvents such as ethyl acetate:toluene, toluene:acetonitrile, hexane:acetone, and the like. Suitable silica gel TLC solvent systems include hexane:acetone, chloroform:methanol, toluene:acetonitrile, and the like. A preferred procedure involves reverse phase HPLC on octadecyl silanized silica gel with an acidified acetonitrile:water eluant. The antibiotic can be detected by bioautography using, for example, *Bacillus subtilis* or by other methods such as, for example, vanillin-sulfuric acid spray reagent or ultraviolet (UV) analysis.

The dehydrohalogenation derivatives of A80915 are those compounds wherein the chlorine substituent alpha to the ketone and an adjacent hydrogen atom are removed to form a double bond. The dehydrochlorination derivatives are prepared by standard dehydrohalogenation reactions. For example, A80915 component A or C is reacted with a salt such as lithium chloride and the like in an organic solvent such as dimethylformamide or the like, or with a base such as sodium hydride, sodium methoxide, sodium hydroxide, sodium carbonate, sodium bicarbonate, or the like, in a polar solvent such as an alcohol, for example, methanol, ethanol, or the like. Alternatively, component A or C can be reacted with an amine, such as trimethylamine, triethylamine, diethylamine, 1,8-diazabicyclo[5.4.0]undec-7-ene (DBU), or 1,5-diazabicyclo[4.3.0]non-5-ene (DBN), and like amines. A preferred procedure utilizes diisopropylethylamine in methanol. The crude product may be purified using standard HPLC techniques.

The dehydrohalogenation derivative of A80915A has the structure:

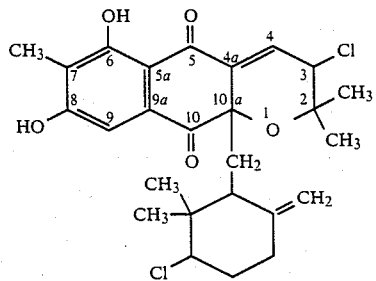

Components A80915B and A80915D will spontaneously lose nitrogen to give A80915A and A80915C, respectively, under a wide variety of conditions, for example, while standing at room temperature in a solvent such as methanol, ethanol or water, and the like. Loss of nitrogen is accelerated by, for example, heating or the addition of salts or mild reducing agents such as sodium hyposulfite, and the like.

The A80915 antibiotics inhibit the growth of bacteria which are pathogenic to animal life. For example, Table III shows the minimal inhibitory concentration (MIC) at which the A80915 antibiotics inhibit certain Gram-positive organisms. The MIC's in Table III were determined by conventional agar-dilution assays.

TABLE III

Antibacterial Activity of A80915 Components and Derivative

| | MIC (mcg/ml) | | | | |
|---|---|---|---|---|---|
| | A | B | C | D | Compound 5 |
| TEST ORGANISM | | | | | |
| *Staphylococcus aureus* X1.1 | 2 | 2 | >128 | 1 | 4 |
| *Staphylococcus aureus* V41 | 2 | 2 | >128 | 2 | 4 |
| *Staphylococcus aureus* X400 | 2 | 2 | >128 | 2 | 4 |
| *Staphylococcus aureus* S13E | 2 | 2 | >128 | 1 | 4 |
| *Staphylococcus epidermis* EPI1 | 2 | 2 | >128 | 2 | 4 |
| *Staphylococcus epidermis* 222 | 2 | 2 | >128 | 1 | 4 |
| *Streptococcus pyogenes* C203 | 32 | 8 | >128 | 2 | 4 |
| *Streptococcus pneumoniae* Park1 | 32 | 8 | >128 | 1 | 4 |
| *Streptococcus faecium* X66 | 2 | 8 | >128 | 32 | 8 |
| *Streptococcus faecium* 2041 | 8 | 8 | >128 | 32 | 8 |
| Gram-negative | >128 | >128 | >128 | >128 | >128 |
| Veterinary Organisms | | | | | |
| Staphylococcus sp. | 0.10 | <0.05 | 1.56 | 0.20 | |
| Streptococcus sp. | 0.20 | 0.10 | 3.12 | 3.12 | |
| *Pasteurella multocida* | 3.12 | 0.20 | 50 | 3.12 | |
| *Pasteurella hemolytica* | >50 | 12.5 | 50 | 12.5 | |
| *Bordetella bronchiseptica* | >50 | >50 | >50 | >50 | |
| *Mycoplasma gallisepticum* | 0.78 | 0.10 | 25 | >50 | |
| *Mycoplasma hyopneumoniae* | 3.12 | 3.12 | >50 | 25 | |
| *Escherichia coli* | >50 | >50 | >50 | >50 | |
| *Salmonella typhimurium* | >50 | >50 | >50 | >50 | |

The A80915 antibiotics also are active against anaerobic bacteria. Table IV shows the MIC's at which the A80915 components inhibit various anaerobic bacteria, as determined by standard agar-dilution assay. End points were read after 24-hour incubation.

TABLE IV

Susceptibility of Anaerobic Bacterial Isolates to A80915 Components

| | MIC (mcg/ml) | | | |
|---|---|---|---|---|
| Anaerobic Bacteria | A | B | C | D |
| *Clostridium difficile* 2994 | 4 | >128 | 8 | 16 |
| *Clostridium perfringens* 81 | 4 | >128 | 8 | 16 |
| *Clostridium septicum* 1128 | 4 | >128 | 8 | 16 |
| *Eubacterium aerofaciens* 1235 | 4 | >128 | 8 | 16 |
| *Peptococcus asaccharolyticus* 1302 | 16 | 128 | 2 | 4 |
| *Peptococcus prevoti* 1281 | 4 | 64 | 2 | 8 |
| *Peptostreptococcus anaerobius* 1428 | >128 | >128 | 4 | 8 |
| *Peptostreptococcus intermedius* 1264 | 4 | 128 | 128 | 128 |
| *Propionibacterium acnes* 79 | 32 | 128 | 4 | 16 |
| *Bacteriodes fragilis* 111 | >128 | >128 | 128 | 16 |
| *Bacteriodes fragilis* 1877 | >128 | >128 | 4 | 16 |
| *Bacteriodes fragilis* 1936B | >128 | >128 | 4 | 8 |
| *Bacteriodes thetaiotaomicron* 1438 | >128 | >128 | >128 | >128 |
| *Bacteriodes melaninogenicus* 1856/28 | 2 | 128 | 64 | 32 |
| *Bacteriodes melaninogenicus* 2736 | >128 | >128 | >128 | >128 |
| *Bacteriodes vulgatis* 1211 | >128 | >128 | >128 | >128 |
| *Bacteriodes corrodens* 1874 | >128 | >128 | >128 | >128 |
| *Fusobacterium symbiosum* 1470 | >128 | >128 | >128 | >128 |
| *Fusobacterium necrophorum* 6054A | >128 | >128 | >128 | 8 |

The A80915 antibiotics also showed antifungal and anti-protozoan activity. The minimum inhibitory concentration (MIC) at which the A80915 components inhibit certain organisms is shown in Table VI.

TABLE VI

Anti-protozoan and Anti-fungal Activity of A80915 Components.

| Test Organism | MIC (mcg/ml) | | | |
|---|---|---|---|---|
| | A | B | C | D |
| Trichomonas vaginalis | 12.5 | 6.25 | >100 | 25 |
| Trichomonas foetus | 50 | 12.5 | >100 | 25 |
| Candida albicans | >40 | 5.0 | >80 | 10 |

The acute toxicity of the A80915 antibiotics in mice, when administered by intraperitoneal injection and expressed as $LD_{50}$, is shown in Table V.

TABLE V

Acute Toxicity of A80915 Components.

| Component | $LD_{50}$ (mg/kg) |
|---|---|
| A | 212 |
| B | 75 |
| C | >300 |
| D | 11.8 |

Pharmaceutical and veterinary formulations of the A80915 antibiotics are also part of this invention. In one aspect, an A80915 antibiotic can be formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers, and the like.

The compositions comprising an A80915 antibiotic will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulation of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble form of the compound can be dissolved and administered in a pharmaceutical diluent such as Water-for-Injection, physiological saline or 5% glucose solution. A suitable insoluble form of the compound may be prepared and administered as a suspension in an aqueous base or a pharmaceutically-acceptable oil base, e.g., an ester of a long chain fatty acid such as ethyl oleate.

For oral use, a sterile formulation of a suitable form of the antibiotic formulated in a diluent such as distilled or deionized water is particularly useful.

Alternatively, the unit dosage form of the antibiotic can be a solution of the antibiotic in a suitable diluent in sterile, hermetically-sealed ampoules. The concentration of the antibiotic in the unit dosage may vary, e.g., from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The animal may be either susceptible to, or infected with, the microorganism. The method comprises administering to the animal an amount of an A80915 antibiotic which is effective for this purpose. In general, an effective amount of A80915 antibiotic is a dose between about 0.5 and about 100 mg/kg. A preferred dose is from about 1 to about 60 mg/kg of active compound. A typical daily dose for an adult human is from about 50 mg to about 1.0 g.

In practicing this method, the antibiotic can be administered in a single daily dose or in multiple doses per day. The treatment regime may require administration over extended periods of time, e.g., for several days or for from one to six weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure, a sterile formulation of a suitable soluble form of the antibiotic is incorporated in a physiological fluid, such as 5% dextrose solution, and the resulting solution is infused slowly IV. Alternatively, the piggyback method of IV infusion can also be used.

For veterinary uses, an A80915 antibiotic also can be administered to animals orally or parenterally. The most practical way to administer the A80915 antibiotics is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A80915 antibiotic directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid or solid preparations.

The final formulation of feeds for animals will depend upon the amount of drug to be administered. The common methods of formulating, mixing, and pelleting feeds may be used to prepare feeds containing an A80915 antibiotic.

The A80915 antibiotics may be formulated for parenteral administration by methods recognized in the veterinary pharmaceutical art. Effective injectable compositions containing the A80915 antibiotics may be in either suspension or solution form. In the solution form, the A80915 antibiotic is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically-acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

In order to illustrate more fully the operation of this invention, the following examples are provided:

EXAMPLE 1

Preparation of Antibiotic A80915 Using Streptomyces aculeolatus

A. Shake-flask Fermentation of *Streptomyces aculeolatus*

The culture *Streptomyces aculeolatus*, NRRL 18422, either as a lyophilized pellet or as a suspension maintained in liquid nitrogen, is used to inoculate a vegetative medium having the following composition:

| Vegatative or Seed Medium | |
|---|---|
| Ingredient | Amount (g/L) |
| Glucose | 10.0 |
| Soluble starch | 20.0 |
| Enzyme-hydrolyzed casein* | 5.0 |
| Yeast extract** | 5.0 |
| CaCO₃ | 1.0 |
| Deionized water | q.s. 1 liter |

*N-Z Amine A, Sheffield Products, Norwich, NY.
**Difco Laboratories
adjusted to 7.5 with sodium hydroxide before sterilization Slants or plates are prepared by adding 2.5% agar to the seed medium. The inoculated slant is incubated at 30° C. for from about 10 to about 14 days. The mature slant culture is scraped with a sterile tool to loosen the spores and remove and macerate the mycelial mat. About one-fourth of the loosened spores and culture growth thus obtained is used to inoculate 50 mL of a first-stage seed medium.

The inoculated first stage medium (50 ml) is incubated in a 250-mL Erlenmeyer flask at 30° C. for 48 to 72 hours on a shaker orbiting in a 2.5-inch (6.4 cm) circle at 250 rpm.

This incubated first stage medium (1.00 mL) is used to inoculate 50 mL of a production medium having the following composition:

| Ingredient | Amount (g/L) |
|---|---|
| Glucose | 10.0 |
| Blackstrap molasses | 20.0 |
| Bacto peptone* | 5.0 |
| CaCO₃ | 2.0 |
| Deionized or Czapek's mineral stock** | 2.0 (ml/L) |
| Deionized or tap water | q.s. 1 liter |

*Difco Laboratories
**Czapek's mineral stock solution:
KCl 100 g
MgSO₄.7H₂O 100 g
FeSO₄.7H₂O 100 g
Deionized water 1000 ml The inoculated production medium is incubated in a 250-mL wide-mouth Erlenmeyer flask at 30° C. for 5 to 6 days on a rotary shaker orbiting in a two-inch circle at 250 rpm.

B. Tank Fermentation of *Streptomyces aculeolatus*

In order to provide a large volume of inoculum, 10 mL of incubated first stage medium, prepared as described in Section A, is used to inoculate 400 mL of a second-stage growth medium having the same composition as that of the vegetative medium. This second-stage medium is incubated in a two-liter wide-mouth Erlenmeyer flask for about 72 hours at 30° C. on a rotary shaker orbiting in a two-inch circle at 250 rpm.

Incubated second-stage medium (400 mL) thus prepared is used to inoculated 100 liters of sterile production medium prepared as described in Section A except that P-2000 (0.1 ml/L) and Sag 471 (0.2 g/L) antifoam agents are added. The inoculated production medium is allowed to ferment in a 165-liter stirred fermentation tank for 4 to 5 days at a temperature of 30° C. The airflow (0.5–1.0 v/v/m) in the stirred vessel (150–200 rpm) is adjusted to maintain a dissolved oxygen level above 30% of air saturation.

EXAMPLE 2

Isolation of A80915 From Mycelium

A. Isolation of A80915

Combined fermentation broth (110 L) from a 10 L and a 100 L fermentation was filtered with the aid of 5% Hyflo Supercel. The mycelial filter cake was extracted with 30 L acetone. The acetone extract was concentrated in vacuo to remove the acetone. The concentrate (6 L) was extracted twice with 3 L ethyl acetate. The pooled ethyl acetate extracts were concentrated in vacuo to dryness to yield 75.4 g of antibiotic A80915.

B. Separation of A80915 Components

A80915 (40 g) from Section A was dissolved in 35 ml methanol. The solution was pumped onto a 2 in. diameter ×60 cm stainless-steel column containing octadecyl silanized silica gel, 20μ (Whatman LP-1). The column was developed using an acetonitrile:H₂O: formic acid gradient:

| Solvent 1 | 70:29.9:0.1 | fractions 1–150 |
|---|---|---|
| Solvent 2 | 80:19.9:0.1 | fractions 151–243 |
| Solvent 3 | 100:0:0 | fractions 244–350 |

Fractions (20 mL) were collected at a flow rate of 17 mL/min. Isolation was monitored by UV absorption with an ISCO UA-5 detector-multiplexer at 254 nm/280 nm, 2.0 AUFS. Fractions containing A80915A (Nos.

281-315) were combined and concentrated to dryness to yield 1.99 g of antibiotic A80915A. Fractions containing A80915C (Nos. 179-205) were combined and concentrated to dryness to yield 1.69 g of antibiotic A80915C.

EXAMPLE 3

Isolation of A80915 From Fermentation Broth

A. Isolation of A80915

Filtered fermentation broth (100 L) was extracted with 40 L ethyl acetate. The ethyl acetate extract was washed with about 4 L water. The water wash was discarded and the ethyl acetate extract was concentrated to dryness to yield 72.85 g of antibiotic A80915.

B. Separation of A80915 Components

A80915 (20 g) from Section A was dissolved in 35 ml methanol. The solution was pumped onto a 2 in. diameter ×60 cm stainless steel column containing octadecyl silanized silica gel, 20μ. The column was developed using an acetonitrile:water:formic acid gradient:

| Solvent 1 | 65:34.9:0.1 | fractions 1-95 |
| Solvent 2 | 70:29.9:0.1 | fractions 96-150 |
| Solvent 3 | 75:24.9:0.1 | fractions 151-244 |
| Solvent 4 | 100:0:0 | fractions 254-350 |

Fractions (18 mL) were collected at a flow rate of 9 mL/min. Isolation was monitored by UV absorption with an ISCO UA-5 detector-multiplexer at 254 nm/280 nm, 2.0 AUFS. Fractions containing A80915A (Nos. 298-310) were combined and concentrated to dryness to yield 0.63 g of antibiotic A80915A. Fractions containing A80915B (Nos. 280-291) were combined and concentrated to dryness to yield 1.11 g of antibiotic A80915B. Fractions containing A80915C (Nos. 208-225) were combined and concentrated to dryness to yield 0.92 g of antibiotic A80915C. Fractions containing A80915D (Nos. 125-143) were combined and concentrated to dryness to yield 1.32 g of antibiotic A80915D.

EXAMPLE 4

Preparation of A80915A Dehydrochlorination Derivative

A solution of A80915A (502 mg, 0.95 mmol) and diisopropylethylamine (830 μl, 5 eq) in methanol (50 ml) was heated at 60° C. under dry $N_2$. After 92 hr, the reaction solution was diluted with EtOAc (150 ml), extracted with 1N HCl (3×100 ml) and brine (1×100 ml), dried ($Na_2SO_4$), and evaporated to dryness. The crude product was purified by preparative reverse-phase HPLC [C18, 1.8 L of MeOH/$H_2O$/$HCO_2H$ (85:14.9:0.1) then 2.2 L of MeOH/$H_2O$/$HCO_2H$ (90:9.9:0.1)] to give 86 mg of the dehydrochlorination derivative as a pale yellow solid.

Ultraviolet (EtOH): $\lambda_{max}$274 nm ($\epsilon$14600), $^1$H NMR (CDCl$_3$): similar to A80915A except δ6.85 (d, H-4) and 4.46 ppm (d, H-3).

Mass spectrometry (FDMS): m/z 493, 495 (M+isotopic cluster).

EXAMPLE 5

Preparation of A80915A From A80915B

A solution of sodium hyposulfite (5% $Na_2S_2O_4$ in $H_2O$, 1.0 ml) was added to A80915B (6.5 mg) dissolved in methanol (2.17 ml). The reaction mixture was stirred at room temperature for 30 minutes, after which deionized water (20 ml) was added and the mixture concentrated under reduced pressure to remove the methanol. The aqueous suspension (about 10 ml) was extracted with ethyl acetate (2×20 ml). The combined extracts were filtered and concentrated under reduced pressure to give A80915A containing a small amount of residual A80915B which can be removed by chromatography as in Example 3B.

EXAMPLE 6

Preparation of A80915C from A80915D

A80915D (6.5 mg) was converted to nearly-pure A80915C using the same conditions as Example 4, with the exception that the reaction was stirred for 1 hr at room temperature. Residual A80915D can be removed by chromatography as in Example 3B.

We claim:

1. Antibiotic A80915 comprising components A, B, C, and D, which have the formulas

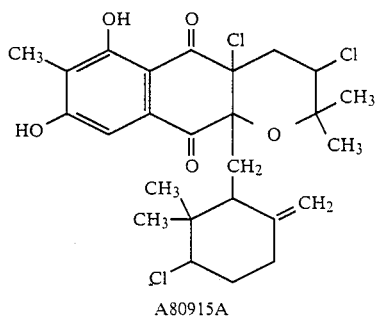

A80915A

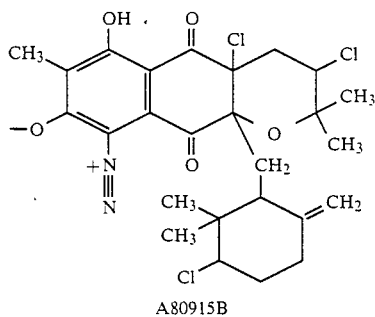

A80915B

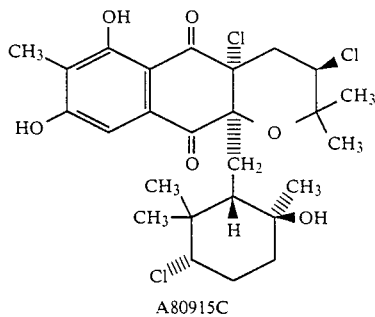

A80915C

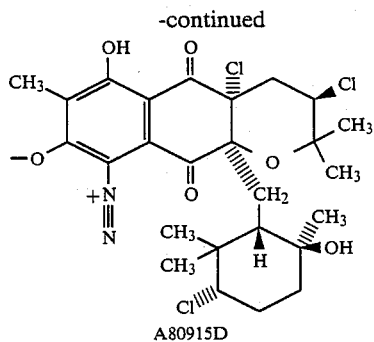

A80915D or a dehydrochlorination derivative of A80915.

2. A compound of claim 1 which is A80915A.

3. A compound of claim 1 which is A80915B.

4. A compound of claim 1 which is A80915C.

5. A compound of claim 1 which is A80915D.

6. A compound of claim 1 which is an A80915 dehydrochlorination derivative of the formula

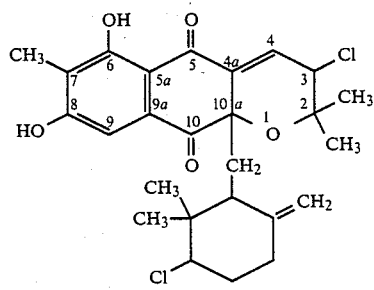

7. Antibiotic A80915 which is produced by culturing *Streptomyces aculeolatus*, NRRL 18422, or an A80915-producing mutant under submerged aerobic conditions in a suitable culture medium until antibiotic A80915 is produced.

8. A process for producing antibiotic A80915 which comprises cultivating *Streptomyces aculeolatus*, NRRL 18422, or an A80915-producing mutant in a culture medium containing assimilable sources of carbon, nitrogen, and inorganic salts under submerged aerobic fermentation conditions until antibiotic A80915 is produced.

9. The process of claim 8 which includes the additional step of separating antibiotic A80915 from the culture medium.

10. The process of claim 9 which includes the additional step of separating component A80915A from antibiotic A80915.

11. The process of claim 9 which includes the additional step of separating component A80915B from antibiotic A80915.

12. The process of claim 9 which includes the additional step of separating component A80915C from antibiotic A80915.

13. The process of claim 9 which includes the additional step of separating component A80915D from antibiotic A80915.

14. The process of claim 8 wherein *Streptomyces aculeolatus*, NRRL 18422, is used.

15. A biologically purified culture of the microorganism *Streptomyces aculeolatus*, NRRL 18422, or a mutant which produces antibiotic A80915 of claim 1.

16. A biologically purified culture of the microorganism *Streptomyces aculeolatus*, NRRL 18422, of claim 15.

17. A composition useful for treating susceptible Gram-positive bacterial infections comprising an effective antibacterial amount of a compound of claim 1 and a suitable vehicle.

18. A method for treating susceptible infections caused by Gram-positive bacteria which comprises administering an effective amount of a composition of claim 17 to an animal.

* * * * *

UNITED STATES PATENT AND TRADEMARK OFFICE
CERTIFICATE OF CORRECTION

PATENT NO. : 4,904,590
DATED : February 27, 1990
INVENTOR(S) : David S. Fukuda, Jon S. Mynderse and Raymond C. Yao It is certified that error appears in the above-identified patent and that said Letters Patent is hereby corrected as shown below:

In Column 1, place the formula numbers 1 and 2 next to Formulas 1 and 2 respectively.

In Column 2, place the formula numbers 3 and 4 next to Formulas 3 and 4 respectively.

In Column 9, place the formula number 5 next to Formula 5 respectively.

In Claim 1, place the formula numbers 1, 2, 3 and 4 next to Formulas 1, 2, 3 and 4 respectively.

In Claim 6, place the formula number 5 next to Formula 5 respectively.

Signed and Sealed this

Twenty-eighth Day of May, 1991

Attest:

HARRY F. MANBECK, JR.

*Attesting Officer*  *Commissioner of Patents and Trademarks*